United States Patent [19]
Ubby

[11] Patent Number: 6,142,949
[45] Date of Patent: Nov. 7, 2000

[54] LEAD PROTECTION AND IDENTIFICATION SYSTEM

[75] Inventor: Johan Ubby, Westport, Conn.

[73] Assignee: Ortivus AB, Taby, Sweden

[21] Appl. No.: 09/200,140

[22] Filed: Nov. 24, 1998

[51] Int. Cl.[7] .............................................. A61B 5/0402
[52] U.S. Cl. ........................................................ 600/508
[58] Field of Search .......................... 437/909; 600/508, 600/372, 386, 394, 522, 509; 128/908

[56] References Cited

U.S. PATENT DOCUMENTS 5,813,404  9/1998  Devlin et al. ........................... 600/372
5,895,298  4/1999  Faupel et al. ........................... 439/909

*Primary Examiner*—George R. Evanisko
*Attorney, Agent, or Firm*—Cooper & Dunham LLP

[57] ABSTRACT

The present invention is a lead protection and identification system for a medical diagnostic device. Electrodes are placed on predetermined locations of a patient, and the system includes clips for attaching to the electrodes. The system identifies a lead and provides information to a user as to which one of the electrodes the lead should be connected to. Potentially dangerous signals are prevented from being inputted to a clip when the clip is not connected to an electrode and prevents the patient from being injured.

12 Claims, 20 Drawing Sheets

LEAD PROTECTION AND IDENTIFICATION SYSTEM

BACKGROUND OF THE INVENTION

1. Field of the Invention

The present invention relates to a medical diagnostic system and, more particularly, to a cable protection and identification system which ensures that each cable of a patient cable bundle is connected to an appropriate electrode and the electrodes are properly placed on predetermined locations of a patient.

2. Description of the Prior Art

It is common today to utilize medical diagnostic systems that have cables which attach to electrodes placed on a patient's body. For example, as shown in FIG. 1A, one type of ECG monitoring device 10 includes a cable bundle 11 having ten individual electrode cables 12, including four limb cables RL, RA, LA and LL and six chest cables, including C1, C2, C3, C4, C5 and C6. Each electrode cable 12 includes a clip (not shown) for connecting to a corresponding electrode 14 provided on a patient 13. Signals received by cables 12 are input via cable bundle 11 to monitoring device 10 and processed for output by audio/visual output 18. The output is used by a doctor, for example, to interpret the function of a patient's heart.

As used herein, the term patient refers to both humans and animals, although in a preferred embodiment patients are humans.

In its basic form, the typical ECG monitoring device 10 includes input processing circuitry 16 for providing functions including analog amplification and conditioning of the signals input via electrode cables 12. The conditioned signals are then input to lead signal processing circuitry 17 which performs functions including processing the signals input by electrode cables 12 and generating the twelve lead waveform signals. The lead waveform signals are then output to audio/visual output 18, which typically includes a display. For example, audio/visual output 18 can include a video monitor or a printer for printing out the lead waveform signals, and can include a tape drive, hard drive or other type of storage device for storing the signals. Input processing circuitry 16 typically monitors each individual electrode cable 12 signal continuously, for detecting pacemaker spikes, noise, 50/60 Hz power noise or loose cables not connected to the electrodes. This information can then also be output by audio/visual output 18 so that an operator can take appropriate action. Typically, in order to minimize the level of noise on the cables 12, each cable 12 is a shielded cable including a signal carrying core wire 20 surrounded by a grounded shield 19. Typically, each of the shields 19 is connected to ground in the ECG monitoring device 10.

Monitoring device 10 will now be explained in more detail below by reference to FIGS. 1B and 1C. Input processing circuitry 16 includes analog processing circuitry 16a, analog to digital converters 16b and digital processing units 16c. As shown, only nine sets of these components are typically necessary, since one limb lead input is typically provided to each analog processing circuit 16a as a common reference input. After processing by circuitry 16a and conversion by converters 16B, the digital signals are input to processing units 16c. Input processing circuitry 16 is capable of monitoring for a loose cable 12, for example, and outputting a signal when one is detected. For example, analog processing circuitry 16a and processing unit 16c can monitor the source impedance which is comprised of the impedance of the supply lines between the electrode 14 and the input processing circuitry 16 as well as the patients tissue impedance and electrode transfer impedance During interruptions, such as may occur when an electrode is removed from the patient, the impedance value will exceed a predetermined upper limit. Upon detecting this event, processing unit 16c will provide an output to controller 17a which in turn can provide an audio and/or visual signal via audio output 18a and signal display 18b.

The processed cable signals output from each of processing units 16c are input to digital lead processing circuitry 17b as shown in FIG. 1C. Digital lead processing circuitry 17b processes the cable signals in a known manner and outputs 12 lead waveform signals to signal display 18b for display to an operator.

Prevention of improperly placed cables and electrodes is important in order to achieve accurate measurements from the patient and to obtain a correct diagnosis. Further, protection of the patient and equipment from unwanted signals entering cables not connected to the patient is desired. One type of conventional cable identification system, as shown in FIG. 1A, is known as a 12 lead electrocardiogram (ECG) monitoring system. Although known as a 12 lead system, as described above, only 10 cables are necessary, with the system creating the 12 lead waveforms from those 10 cable inputs. This known system includes a 10-cable ECG cable bundle 11 in which each of the ECG cables 12 are marked with an electrode identifier label which indicates the respective electrode to which each of the ECG cables should be connected. For example, the 4 limb lead cables are marked RA, LA, RL, LL, respectively and the 6 chest lead cables are marked C1, C2, C3, C4, C5 and C6, respectively. As is well known in the art, each cable 12 is connected to a corresponding one of ten (10) electrodes 14 attached to the patient 13 at predetermined positions, as shown. In this manner, the cables 12 are typically marked to identify the electrode 14 on the patient 13 to which each cable 12 is to be connected. Similarly, for an 8-lead vector electrocardiogram (VCG) cable 21, as shown in FIG. 2, the leads 22 are marked RL, I, A, H, E, C, M and F. For another 8-lead VCG cable, not shown, the leads 22 are marked RL, RA, LA, LL, Neck, Chest, 45 degrees and Back.

Under non-stressful conditions, these conventional systems including marked cables have achieved a certain amount of success at reducing the number of improperly placed cables. However, under stressful conditions which may occur frequently in a medical environment, it may be difficult to quickly read or understand the text on the labels placed on the ECG cable. This can result in the ECG cable being connected to the wrong electrode.

Accordingly, there is a need for an identification system for preventing improperly placed cables on a patient. Such a system will assist in obtaining accurate measurements and correct diagnosis of patients.

Further, conventional systems are susceptible to unwanted signals entering cables not connected to the patient. That is, loose ECG cables may come in contact with nearby power sources such as other medical equipment and unwanted signals may damage the input electronics attached to the patient cable and stray DC or AC current may be distributed into the input electronics and even into the patient.

SUMMARY OF THE INVENTION

An object of the present invention is to provide a cable lead identification system for identifying the correct electrodes to connect to the cable leads of a patient cable.

Another object of the present invention is to provide an electrode detection system for identifying the proper location on the patient on which to connect the electrodes.

Yet another object of the present invention is to provide a lead detection system and electrode detection system for providing an audio or visual message for identifying the correct electrodes to which to connect the leads of a patient cable and the proper locations on the patient to connect the electrodes.

Still another object of the present invention is to provide a lead detection and protection system for preventing patient and equipment from receiving potentially harmful electrical signals.

An aspect of the present invention is a lead identification system comprising a medical diagnostic device, a patient cable having a first end connected to the medical diagnostic device and a second end including a plurality of leads and a plurality of clips each attached to a corresponding one of the plurality of leads. Each clip comprises an input line, a shield, a switch, a handle, and an electrode connector. The switch is operable by the handle and connects the input line to the shield in an inactive mode, and connects the input line to the electrode connector in an active mode. A signal generator provides a predetermined signal to the shield of each clip. A signal analyzer analyzes a signal present on each input line and outputs an analyzing result. A notification device receives the analyzing result output by the signal analyzer and provides information to an operator as to which electrode a given clip should be attached to, based on the analyzing result, the notification device providing the information to the operator when the handle of one of the plurality of clips is pressed and the switch goes from an inactive mode to an active mode, permitting the electrode connector to engage one of the plurality of electrodes. The information provided by the notification device can be an audio message and/or a visual message displayed on a display.

According to another aspect of the present invention, a lead identification system comprises a cable having a first end and a second end, the first end connecting to a device and the second end comprising a plurality of leads. Each of the plurality of leads respectively connects to one of a plurality of electrodes. A plurality of switches are attached to the plurality of leads, respectively, each of the plurality of switches comprising an input line, a shield, an electrode connector, and an activation portion. The switch connects the input line to the shield in an inactive mode, and connects the input line to the electrode connector in an active mode. A signal generator provides an input signal to the shield allowing the switch to selectively cause a characteristic event to occur on the input line. A plurality of clips are attached to the plurality of leads, respectively. An identifier identifies which one of the plurality of clips is in the active mode. A notification device provides information to a user as to which one of the plurality of clips should be connected to which one of the plurality of electrodes. The notification device provides information to the user when the activation portion of one of the plurality of switches is activated and the switch goes from an inactive mode to an active mode.

Another aspect of the present invention relates to an electrode identification system comprising a cable having a first end and a second end, the first end connecting to a device and the second end comprising a plurality of leads. The plurality of leads are connected to a plurality of electrodes, respectively, each of the plurality of electrodes to be placed at predetermined locations. A plurality of switches are attached to the plurality of leads, respectively, and each of the plurality of switches comprises an input line, a shield, an electrode connector, and an activation portion. The switch connects the input line to the shield in an inactive mode, and connects the input line to the electrode connector in an active mode. A signal generator provides an input signal to the shield allowing the switch to selectively cause a characteristic event to occur on the input line. An identifier identifies which one of the plurality of switches is in the active mode. A notification device provides information to a user as to the predetermined locations where the plurality of electrodes and corresponding leads should be placed. The notification device provides the information to the user when the activation portion of the switch is activated and the switch goes from an inactive mode to an active mode.

Still another aspect of the present invention relates to a lead protection and identification system for a medical diagnostic device including a patient cable having a first end and a second end, wherein the first end connects to the medical diagnostic device and the second end includes a plurality of leads, each of the plurality of leads respectively connects to one of a plurality of electrodes, and the plurality of electrodes are placed on predetermined locations of a patient. The lead protection and identification system comprises a plurality of clips attached to the plurality of leads, respectively, each of the plurality of clips comprising an input line, a shield, a switch, a handle, and an electrode connector. The switch is operable by the handle and connects the input line to the shield in an inactive mode, and connects the input line to the electrode connector in an active mode. A signal generator provides an input signal to the shield allowing the switch to selectively cause a characteristic event to occur on the input line. An identifier identifies which one of the plurality of clips is in the active mode based upon the occurrence of the characteristic event of the input line. A notification device provides information to a user as to which one of the plurality of clips should be connected to which one of the plurality of electrodes. The switch of the clip prevents potentially dangerous signals from being inputted to the clip when the clip is not connected to the electrode.

BRIEF DESCRIPTION OF THE DRAWINGS

A more complete appreciation of the present invention and many of the attendant advantages thereof will be readily obtained as the same becomes better understood by reference to the following detailed description when considered in connection with the accompanying drawings, wherein.

DETAILED DESCRIPTION

Figure 1A:
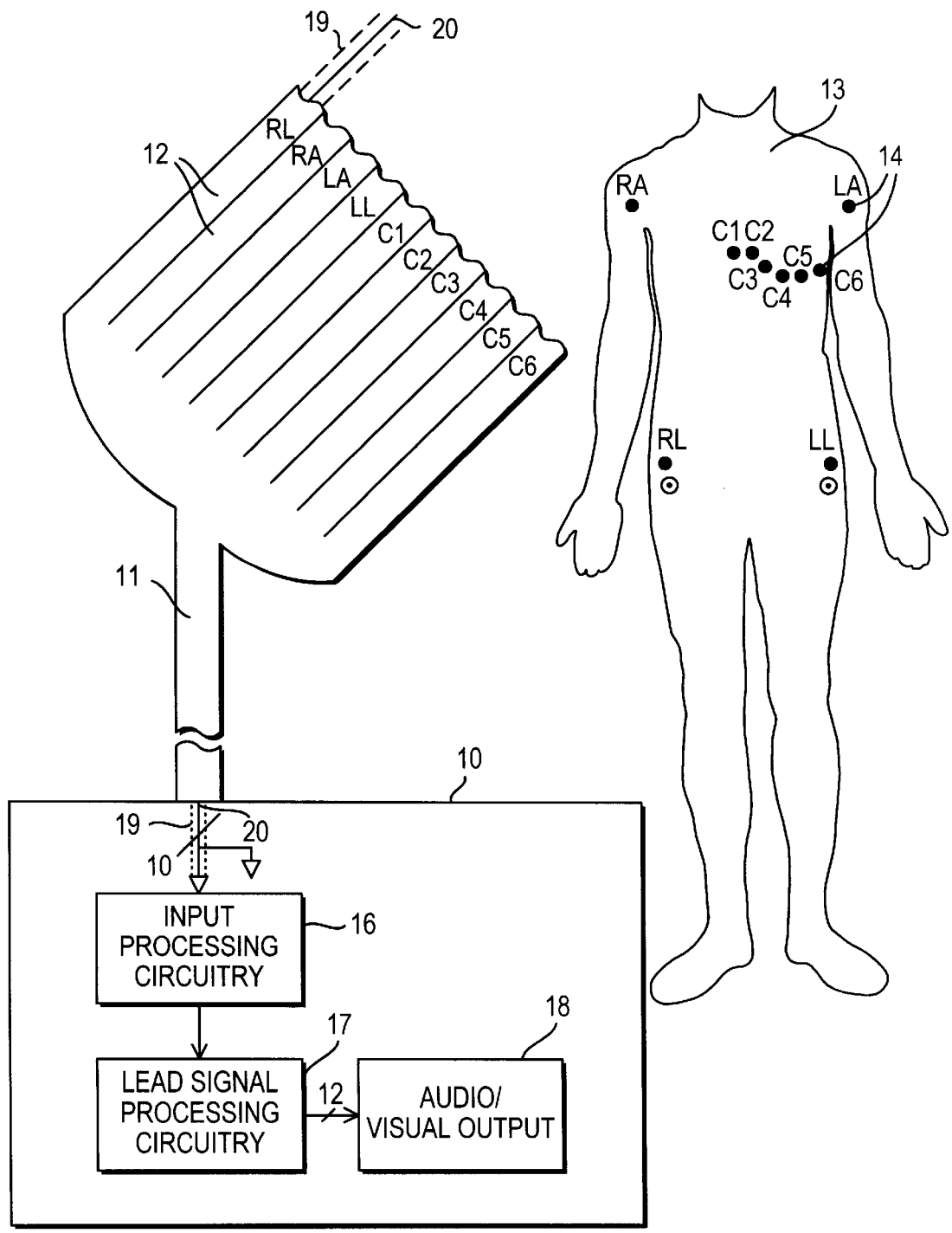
FIGS. 1A–1C illustrate a conventional patient electrode placement system for an ordinary 12-lead ECG recording.

The embodiments of the present invention are described below with reference to the accompanying drawings, in which like reference numerals represent the same or similar elements. In describing the preferred embodiments illustrated in the drawings, specific terminology is employed for the sake of clarity. However, the invention is not intended to be limited to the specific terminology so selected and it is to be understood that each specific element includes all technical equivalents which operate in a similar manner.

Figure 3A:
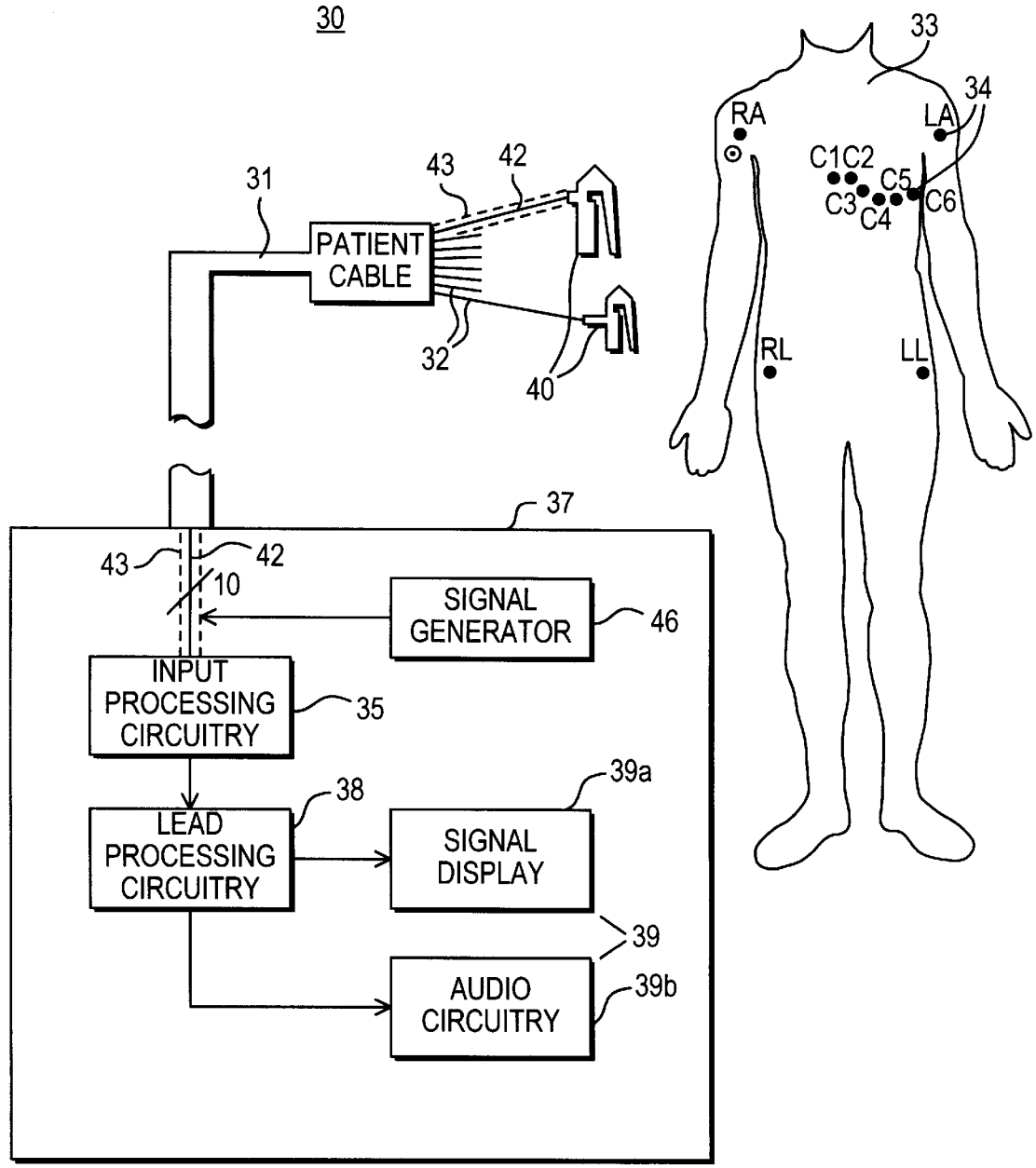
FIGS. 3A–3C illustrate a first embodiment of the present invention.
Figure 3B:
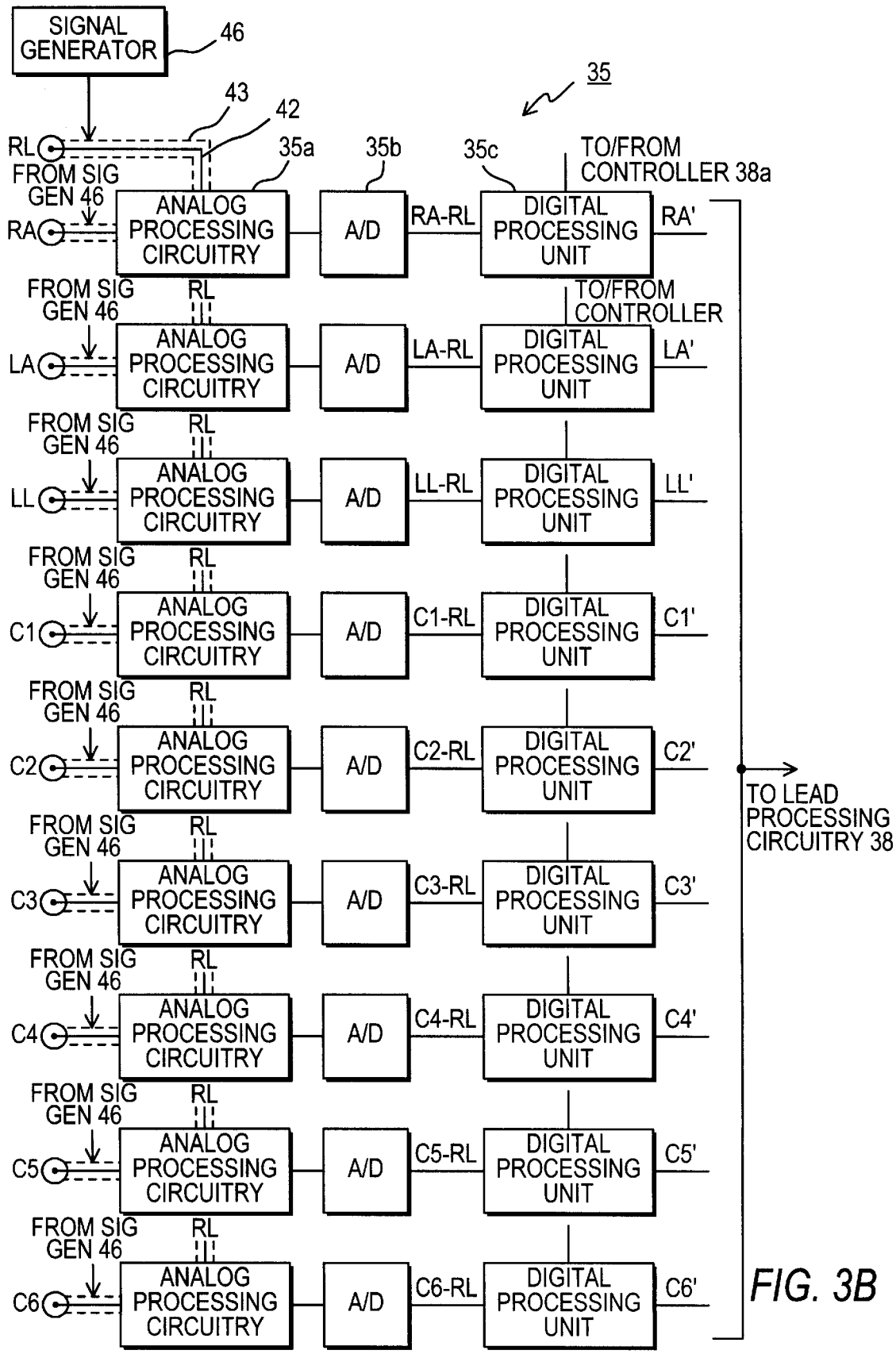
Figure 3C:
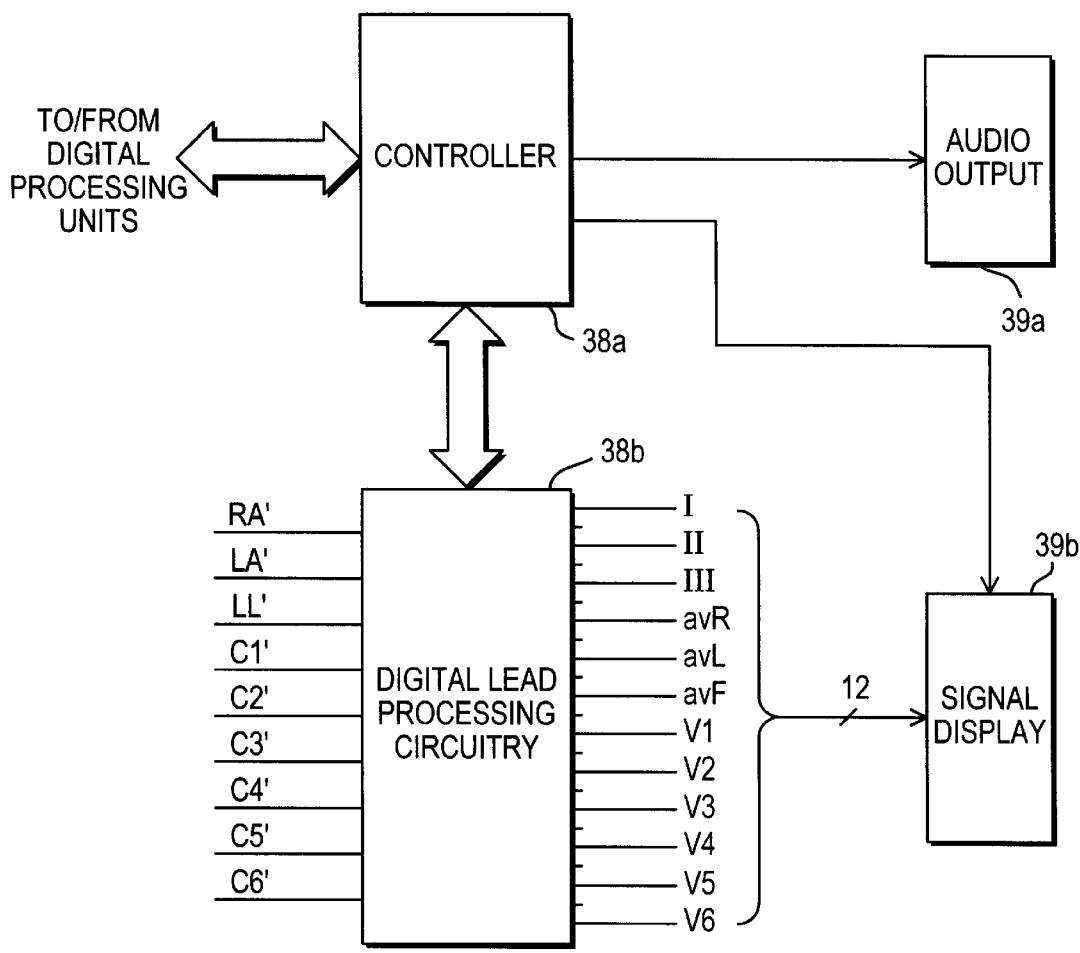

FIGS. 3A–3C illustrate a lead protection and identification system according to a first embodiment of the present invention. Lead protection and identification system 30 is capable of identifying which cable 32 an operator is ready to hook up and notifying the operator exactly which electrode 34 the cable 32 should be connected to.

Cable lead protection and identification system 30 includes a patient cable 31 having a first end and a second end and a diagnostic monitoring device 37. The diagnostic monitoring device 37 may be, for example, a bedside unit to aid in the diagnosis of the cardiac activity of a patient. In a preferred embodiment, the patient cable 31 is a 10-cable ECG bundle for an ordinary 12-lead ECG recording. Other patient cables 31 may also be included within the scope of the present invention including, but not limited to, an 8-lead VCG cable for an 8-lead VCG recording. The first end of the patient cable 31 connects to diagnostic monitoring device 37 and the second end includes a plurality of cable leads 32. Each cable lead 32 includes a signal carrying wire 42 surrounded by a shield 43. Each of the plurality of cable leads 32 includes a clip 40 which respectively connects to a corresponding one of a plurality of electrodes 34 placed on predetermined locations of a patient 33.

Figure 1B:
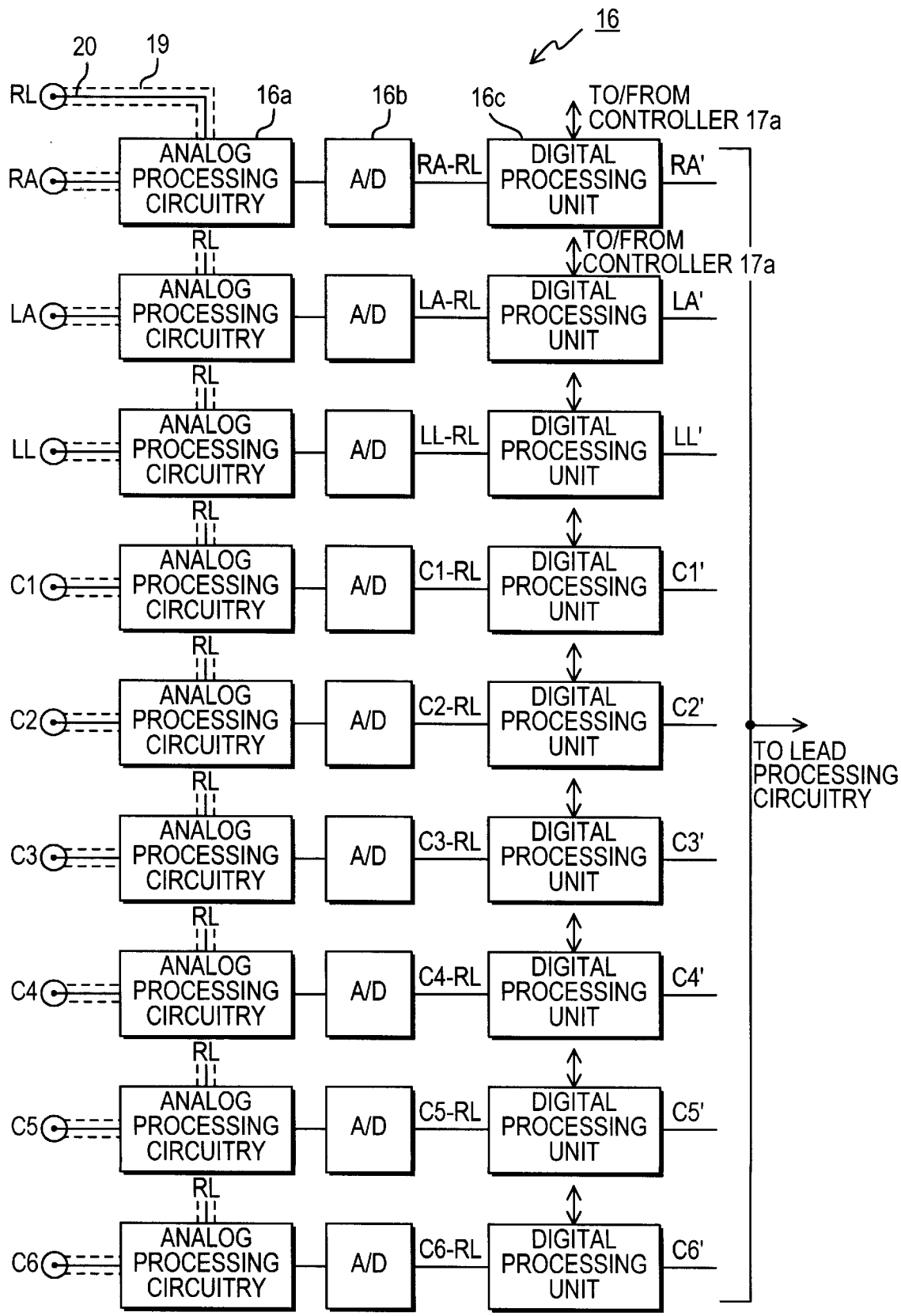
Figure 1C:
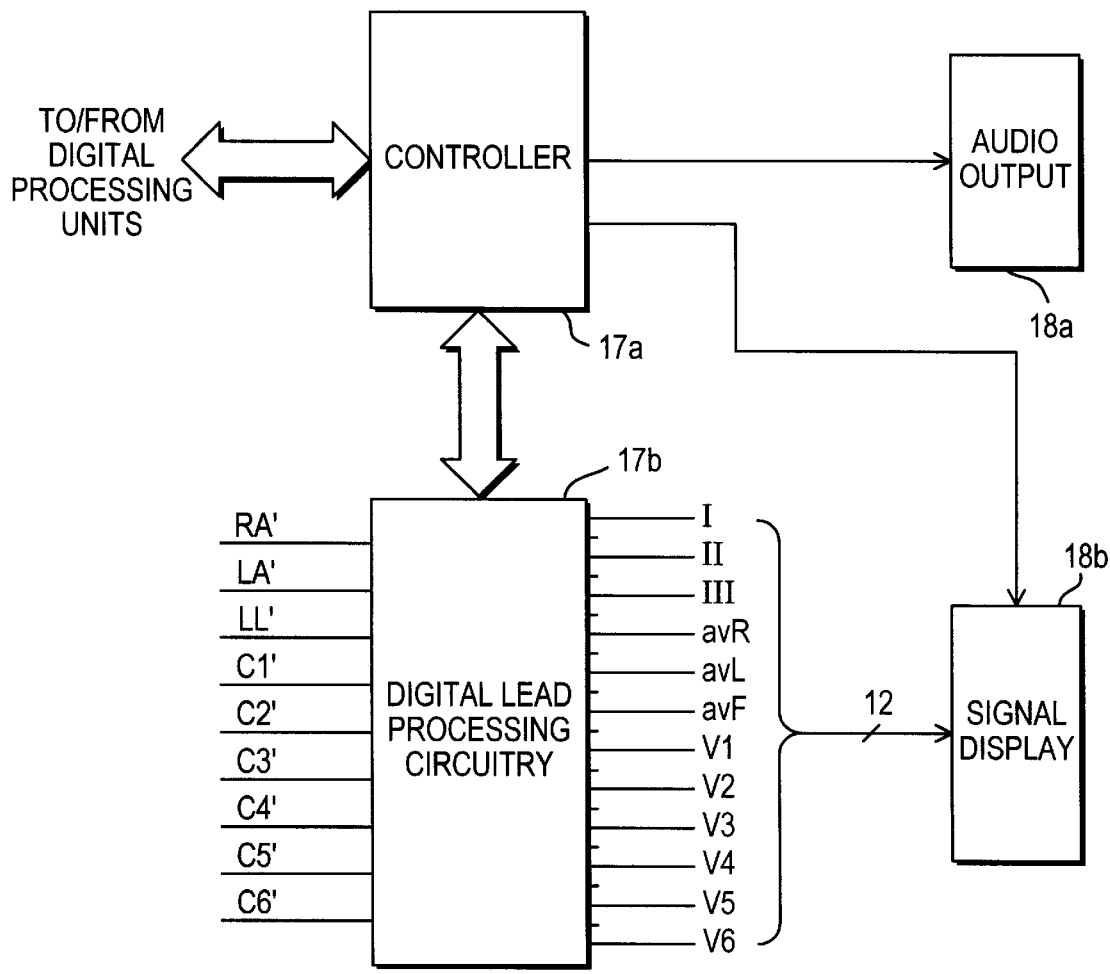
Figure 2:
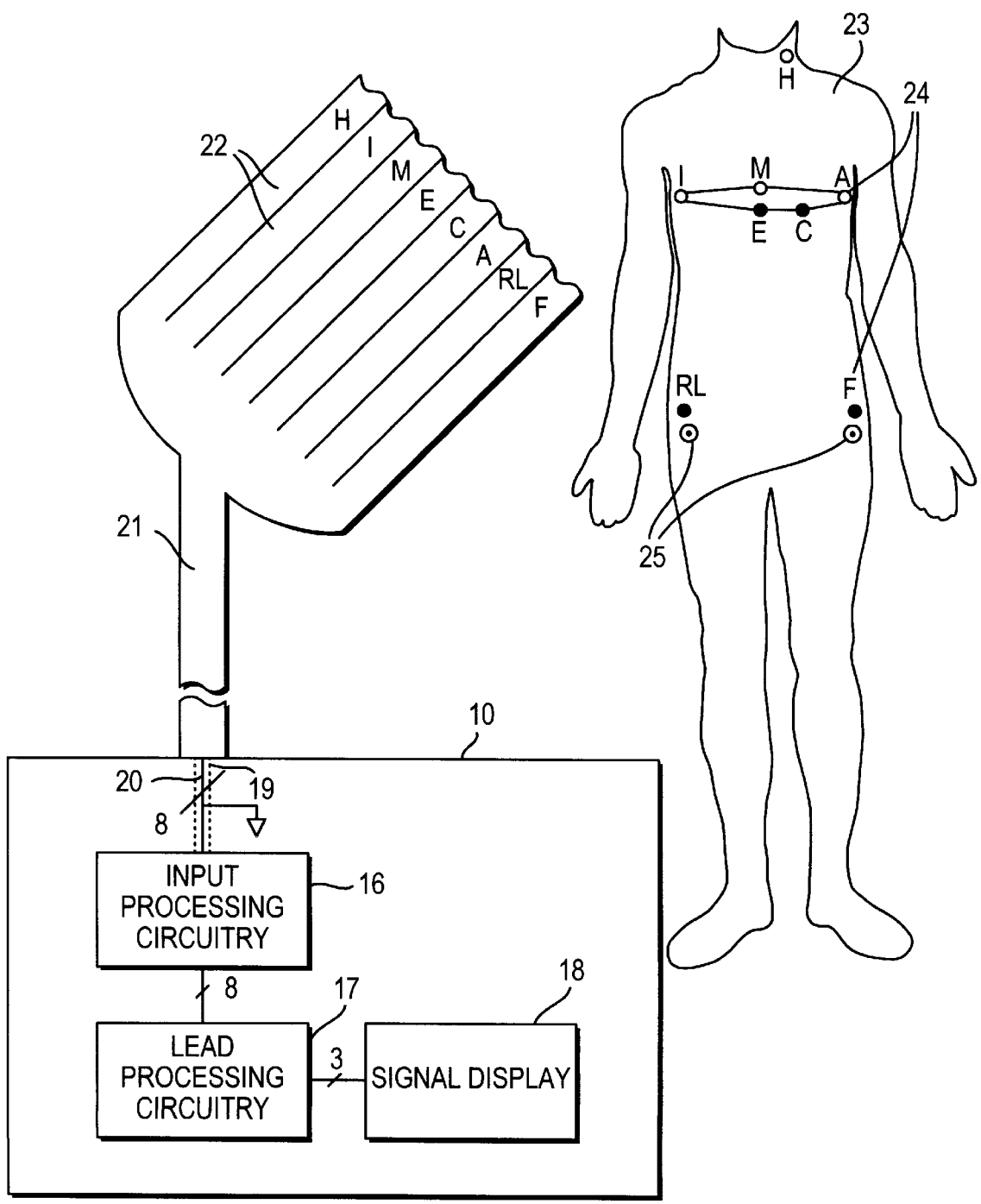
FIG. 2 illustrates a conventional patient electrode placement system for an ordinary 8-lead VCG recording.

The cable lead protection and identification system 30, as shown in FIG. 3A, also includes a signal generator 46 for providing a predetermined signal on the shield 43 of each cable lead 32. (Only one of the twelve shielded wires 32 is shown in FIG. 3A for simplicity of illustration.) As shown in FIGS. 3B and 3C, system 30 includes processing circuitry 35a, A/D converters 35b, processing units 35c, controller 38a, lead processing circuitry 38b, audio output 39a and signal display 39b. Each of these elements is capable of performing at least each of the same functions as described above with respect to the corresponding elements described in FIGS. 1A–1C, as well as additional functions as will be described below.

In a preferred embodiment, the lead protection and identification system 30 is for an ordinary 12-lead ECG recording of a human. In another embodiment, the lead protection and identification system is for an 8-lead VCG recording of a human. The positioning of the electrodes and cable leads for these types of systems is well known in the art.

Figure 4A:
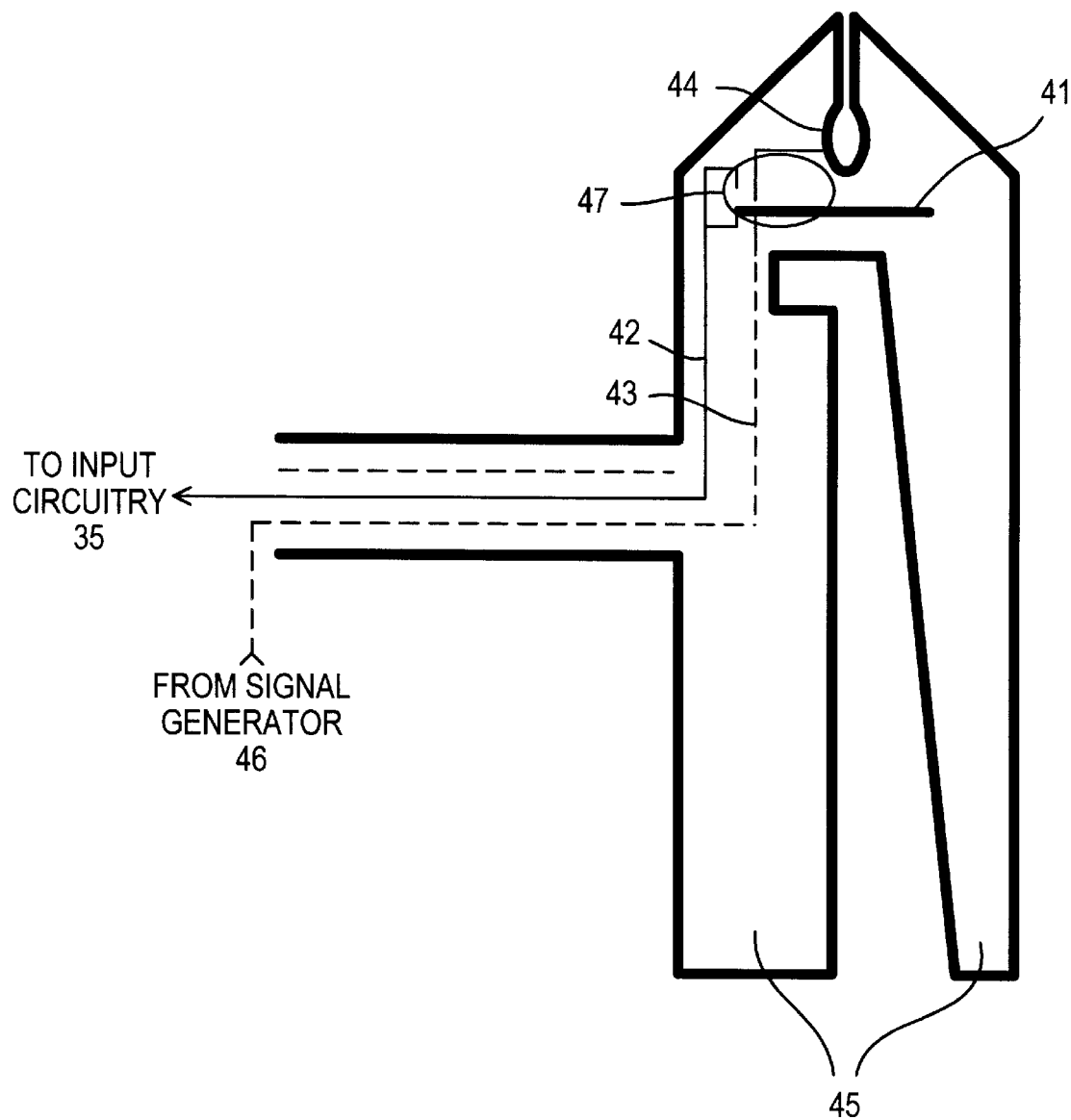
FIG. 4A illustrates one embodiment of a clip according to the present invention incorporating a pin switch in the inactive mode.
Figure 4B:
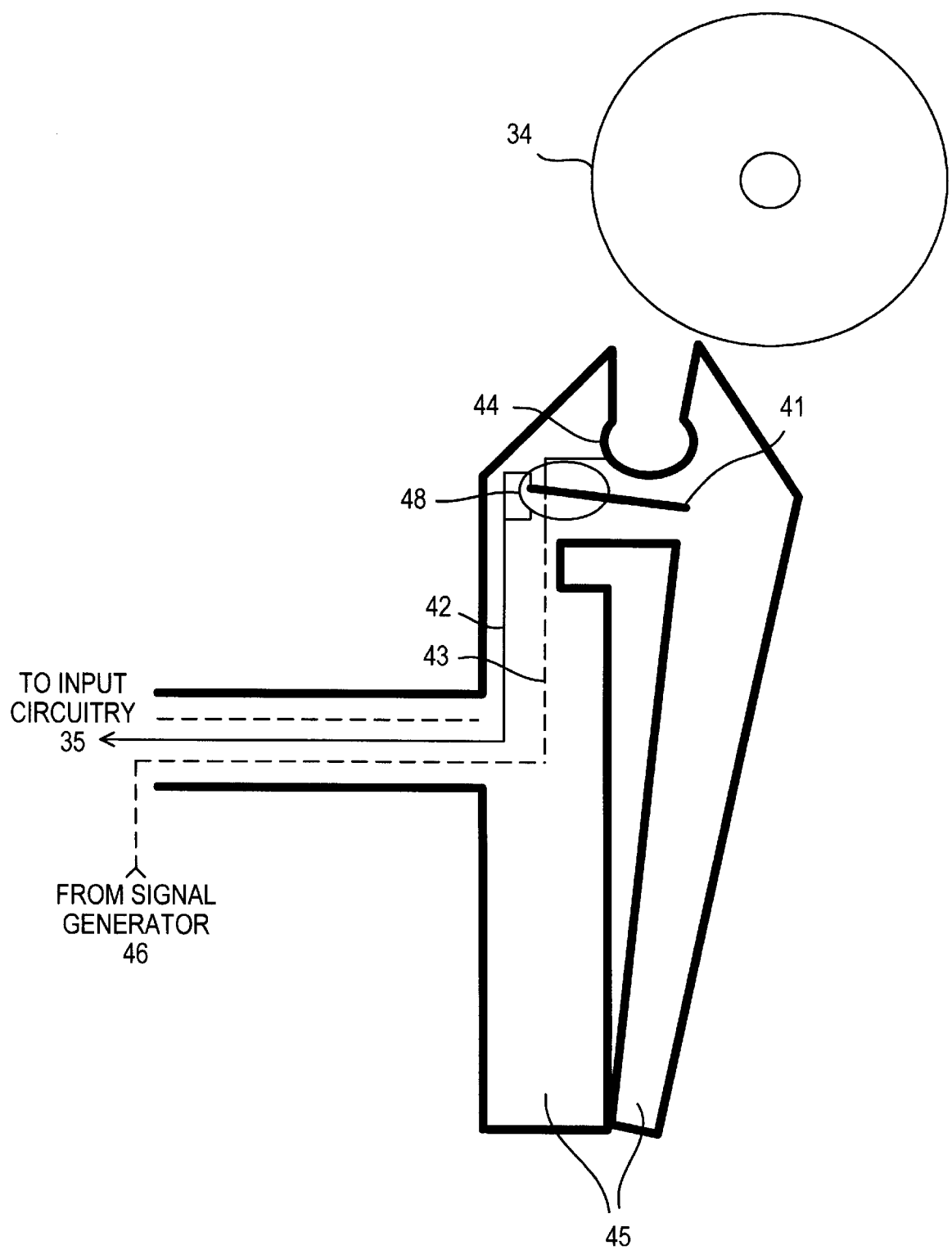
FIG. 4B illustrates the clip according to FIG. 4A incorporating a pin switch in the active mode.
Figure 4C:
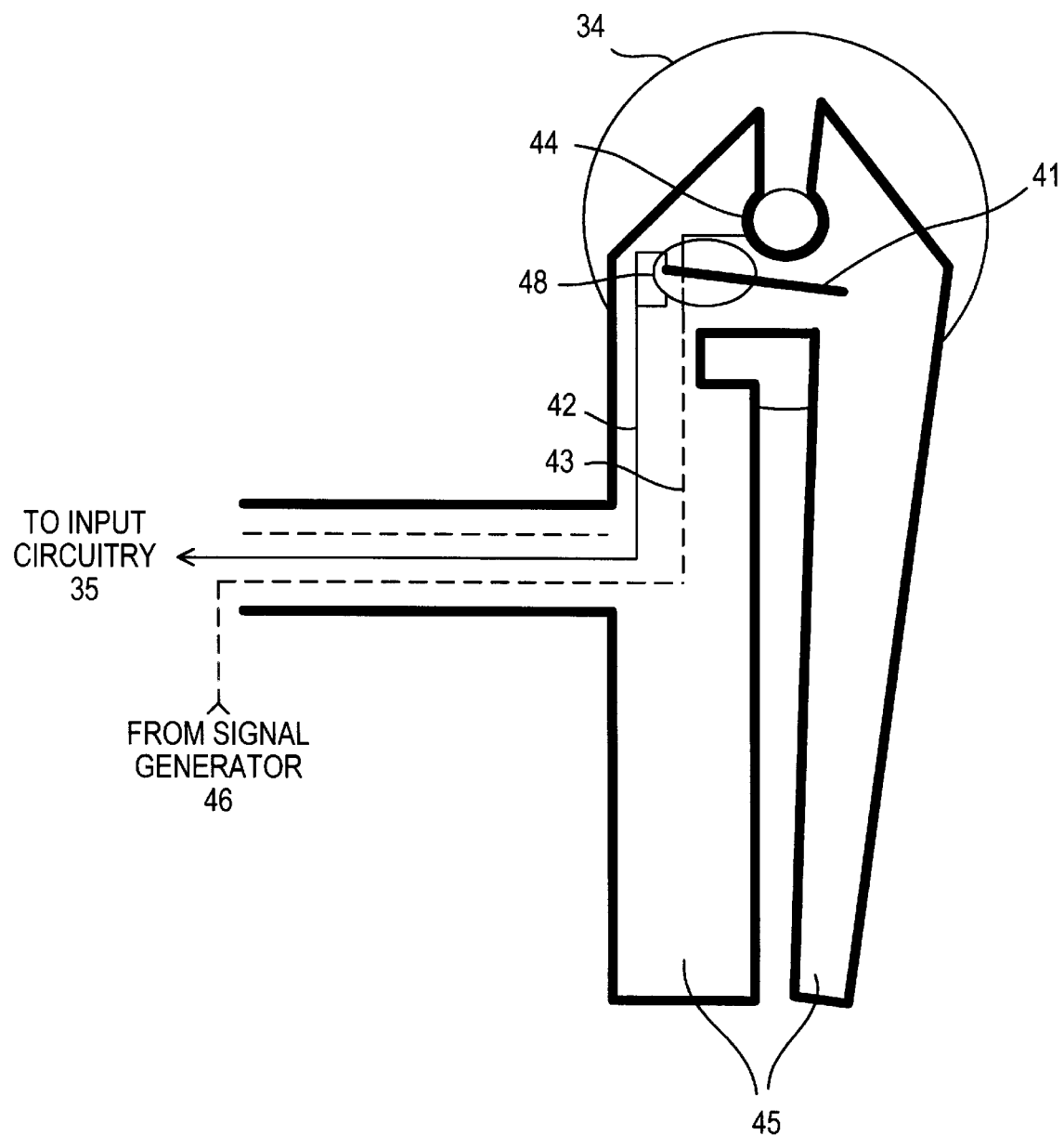
FIG. 4C illustrates the clip according to FIG. 4A incorporating a pin switch in the active mode and the clip connected to an electrode.

Referring now to FIGS. 4A–4C, each of the plurality of clips 40 includes an input line 42 electrically connected to input circuitry 35, a shield 43 electrically connected to signal generator 46, a switch 41, a handle 45, and an electrode connector 44. Switch 41 is normally in the inactive position 47 shown in FIG. 4A and connects the input line 42 to the shield 43. When handle 45 is pressed to ready the clip to be attached to electrode 34, for example, the switch 41 connects the input line 42 to the electrode connector 44 in an active mode 48, as illustrated in FIG. 4B. As shown in FIG. 4C, the switch 41 is maintained in the active mode 48 when the clip is connected to an electrode 34.

Signal generator 46, according to an embodiment of the present invention, outputs to each shield 43 a fixed low voltage DC signal. When in the inactive mode 47 illustrated in FIG. 4A, switch 41 routes the signal on shield 43 to input line 42 and back to input circuitry 35 in monitoring device 37. The signal is then processed by input circuitry 35 and analyzed by lead signal processing circuitry 38. When in the active mode 48, illustrated in FIGS. 4B and 4C, switch 41 routes the signal from electrode connector 44 to input line 42 and back to input circuitry 35 in monitoring device 37.

Figure 5:
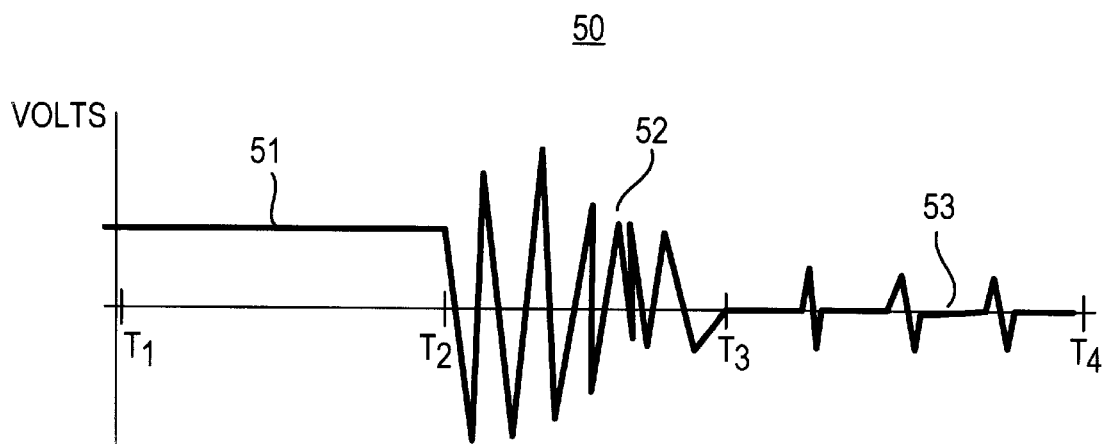
FIG. 5 illustrates an input signal according to an embodiment of the present invention.

FIG. 5 illustrates the signal present on input line 42 of any given cable lead 32 at specific points of time, as measured at the monitoring device 37. The time period from $t_1$ to $t_2$ represents a signal portion 51 present on input line 42 of a given cable lead 32 when the corresponding switch 41 is in the inactive mode 47, as shown in FIG. 4A. Signal portion 51 is formed by the DC voltage signal from the signal generator 46, which is wrapped around via the shield 43 and the switch 41, and returned to monitoring device 37 when switch 41 is in the inactive mode 47.

At time $t_2$, when the handle 45 of the clip 40 is adequately pressed by an operator, the switch 41 goes from the inactive mode 47 to the active mode 48 as shown in FIG. 4B. During time $t_2$ to $t_3$, a signal portion 52 is present on the given cable lead. This represents the input signal in the active mode 48, prior to the clip 40 being connected to the electrode 34. Since clip 40, and more specifically, input line 42 is not electrically connected to an electrode 34 or to the shield 43 at this time, the input on line 42 is floating and the input signal 52 therefore represents a noise signal.

At time $t_3$, the clip 40 is connected to an electrode 34 by the operator and switch 41 remains in the active mode 48 while the clip 40 is connected to the electrode 34, as shown in FIG. 4C. During the time period from $t_3$ to $t_4$, a signal portion 53 represents the input signal in the active mode 48 while the clip 40 is connected to the electrode 34. That is, $t_3$ to $_4t$ represents the time period during which a patient is actually being monitored. At time $t_4$, the clip 40 is disconnected from the electrode 34.

The switch 41 of the first embodiment may be a pin switch 41 integrated with the clip 40, as illustrated in FIGS. 4A–4C, in which the right side of the pin may be molded to the clip 40 allowing the left side of the pin to move when the handle 45 of the clip 40 is adequately pressed, that is, with enough force to cause the pin switch 41 to move from contacting the shield 43 to contacting the electrode connector 44, as shown in FIG. 4C.

Returning to FIGS. 3B and 3C, processing circuitry 35a and units 35c are capable of monitoring the signal on the corresponding cable lead for noise or for a high impedance condition. However, in addition, according to this embodiment of the present invention, each processing unit 35c is programmed to recognize that when a steady DC level (signal 51, FIG. 5) is present on the input line 42, the corresponding clip is in the inactive mode 47 shown in FIG. 4A. Then, when the cable signal switches to the noisy signal level (signal 52, FIG. 5), this event is recognized by the processing unit 35c and a control signal is sent to controller 38a. Controller 38a then outputs an audio signal, such as a digital voice signal via audio output 39a indicating to which electrode 34 that cable should be attached. This information can also be output to the signal display 39b to provide a visual indication to the operator.

In other words, when input processing circuitry 35 detects a steady DC level signal 51 as shown in FIG. 5 on each of the cable inputs, controller 38a determines that lead continuity is good and that no action has yet been taken by an operator with respect to any of the cables 32. Then, when an operator squeezes the handles 45 of the clip 40 in anticipation of attaching the clip 40 to an electrode 34, controller 38a can detect this event from the characteristic signal 52 now present on that input cable 32. At this time, controller 38a outputs an appropriate indication to the user informing the user which electrode 34 that cable clip should be connected to.

Figure 6:
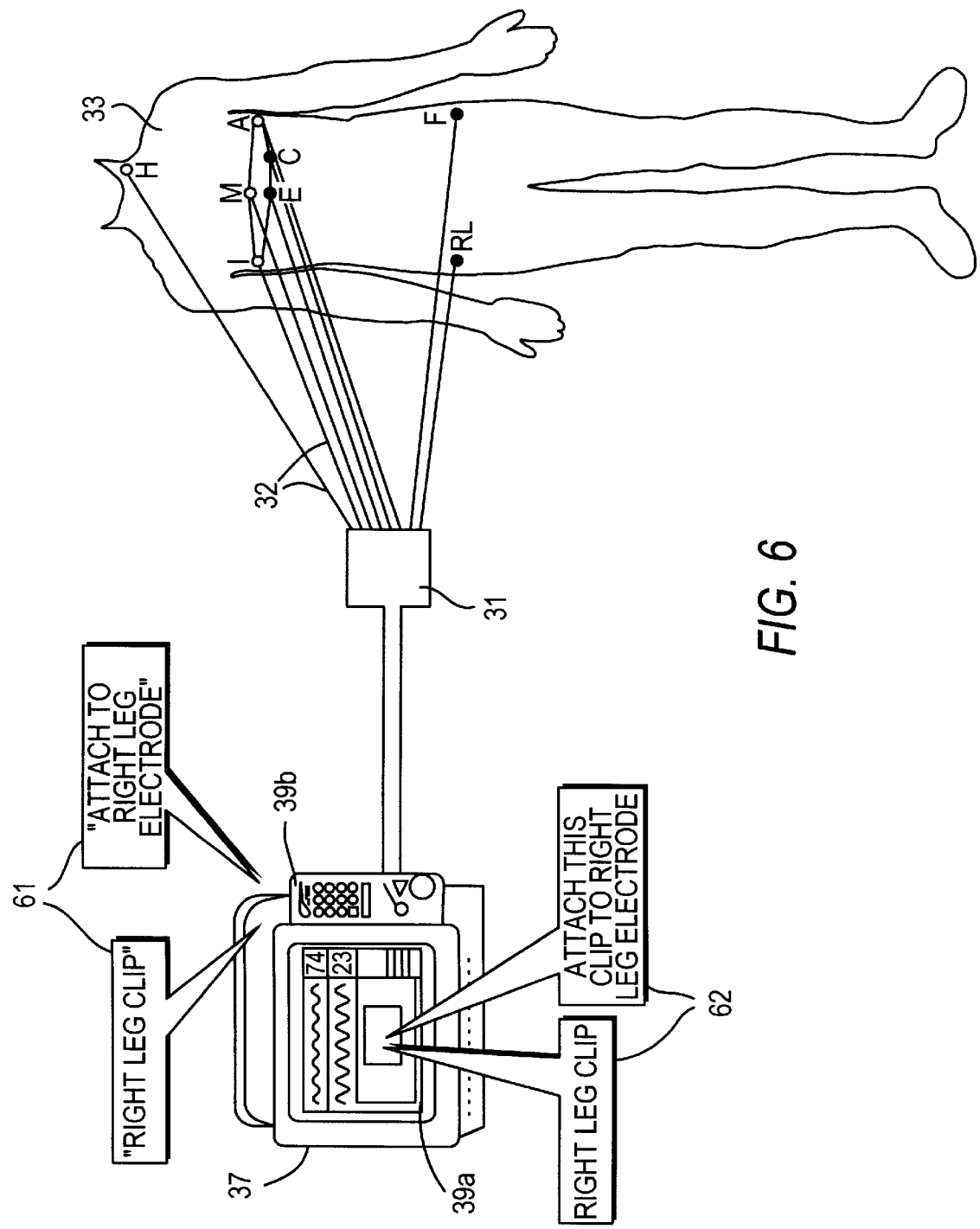
FIG. 6 illustrates an embodiment of a notification device of the present invention.

The user may be a doctor, nurse, medical technician or patient. As shown in FIG. 6, the information output to the user may be in the form of an audio message 61 from audio circuitry 39a and/or a visual message 62 displayed on a display 39b. The audio message 61 will notify the user as to which one of the plurality of electrodes 34 the active cable 32 should be connected. Even in stressful situations, such audio and visual messages allow the user to correctly connect each cable 32 to the appropriate electrode 34 in an easy and timely manner. An audio message 61 allows the user's attention to be directed towards the patient 33 at all times during the connection of cables 32. Further, the audio message 61 and/or visual message 62 allow other individuals to supervise the user's connection of cables 32. The system thus provides the information to the user when the handles 45 of each of the plurality of clips 40 is adequately pressed, and the switch 41 switches from an inactive mode 47 to an active mode 48, so that the user can be directed to place each clip 40 on an appropriate one of the plurality of electrodes 34.

Additionally, the switch 41 of the clip 40 prevents potentially dangerous signals from being inputted to the clip 40 when the clip 40 is not connected to the electrode 34. Potentially dangerous signals may be provided by medical equipment in close proximity to the clip 40. As shown in FIG. 4A, the switch 41 remains in an inactive state 47 when not connected to the electrode 34 and adequate pressure is not placed on the handle 45 of the clip 40. In the inactive state 47, the input line 42 is connected to the shield 43. The input line 42 is thus not connected to the exposed electrode connector 44 in the inactive state 47. Accordingly, any loose clips 40 which may accidently contact a stray voltage and/or current source, will not transfer the voltage or current back to the monitoring device 37 and/or patient 33. The patient 33 and monitoring device 37 are thus protected from injury or damage. In addition, as noted above, the system can monitor the continuity of each lead, to determine, for example, if a lead wire 42 has been broken, by monitoring for the DC level signal 51.

Figure 7A:
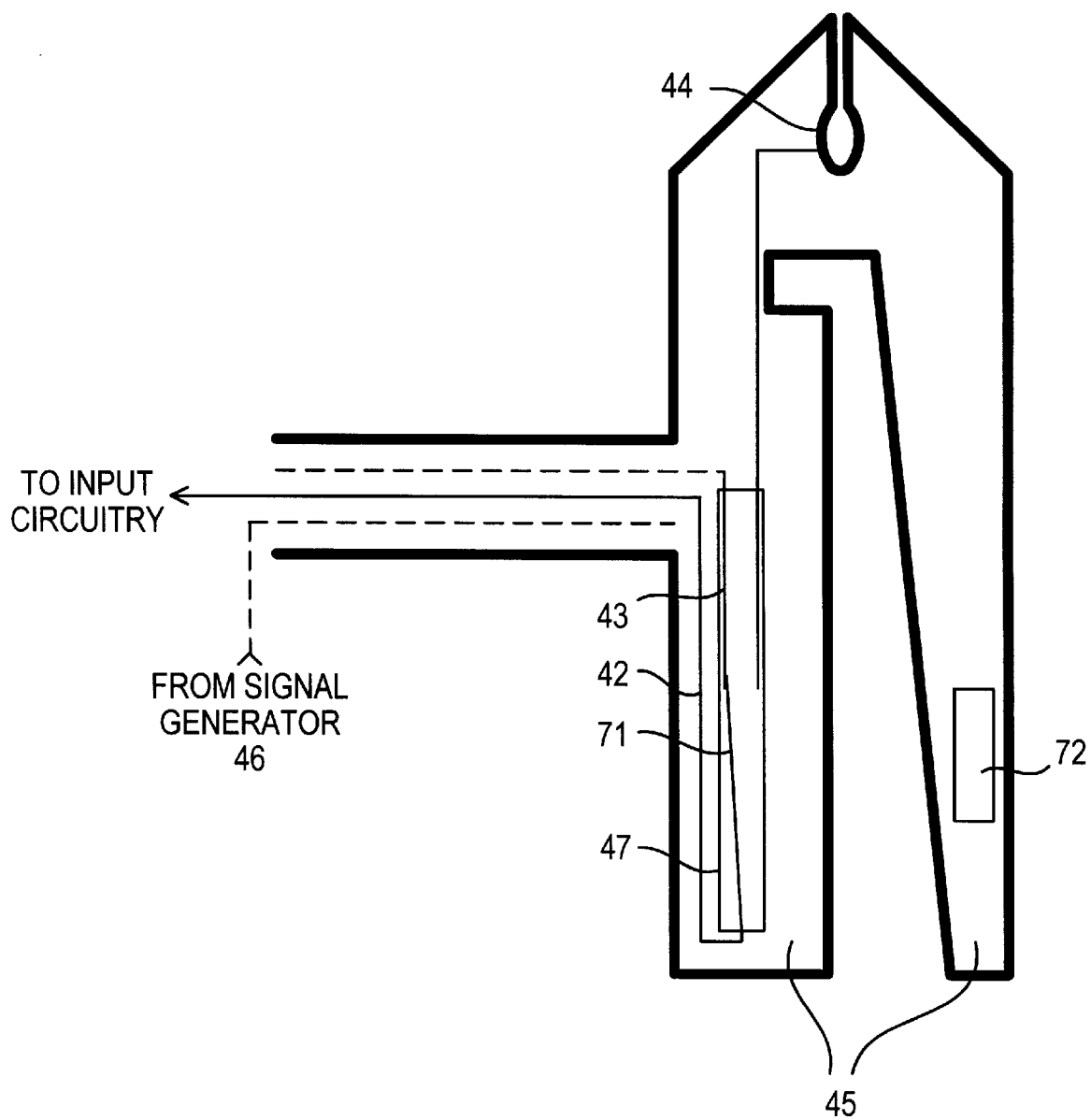
FIG. 7A illustrates another embodiment of a clip according to the present invention incorporating a magnetic reed switch in the inactive mode.
Figure 7B:
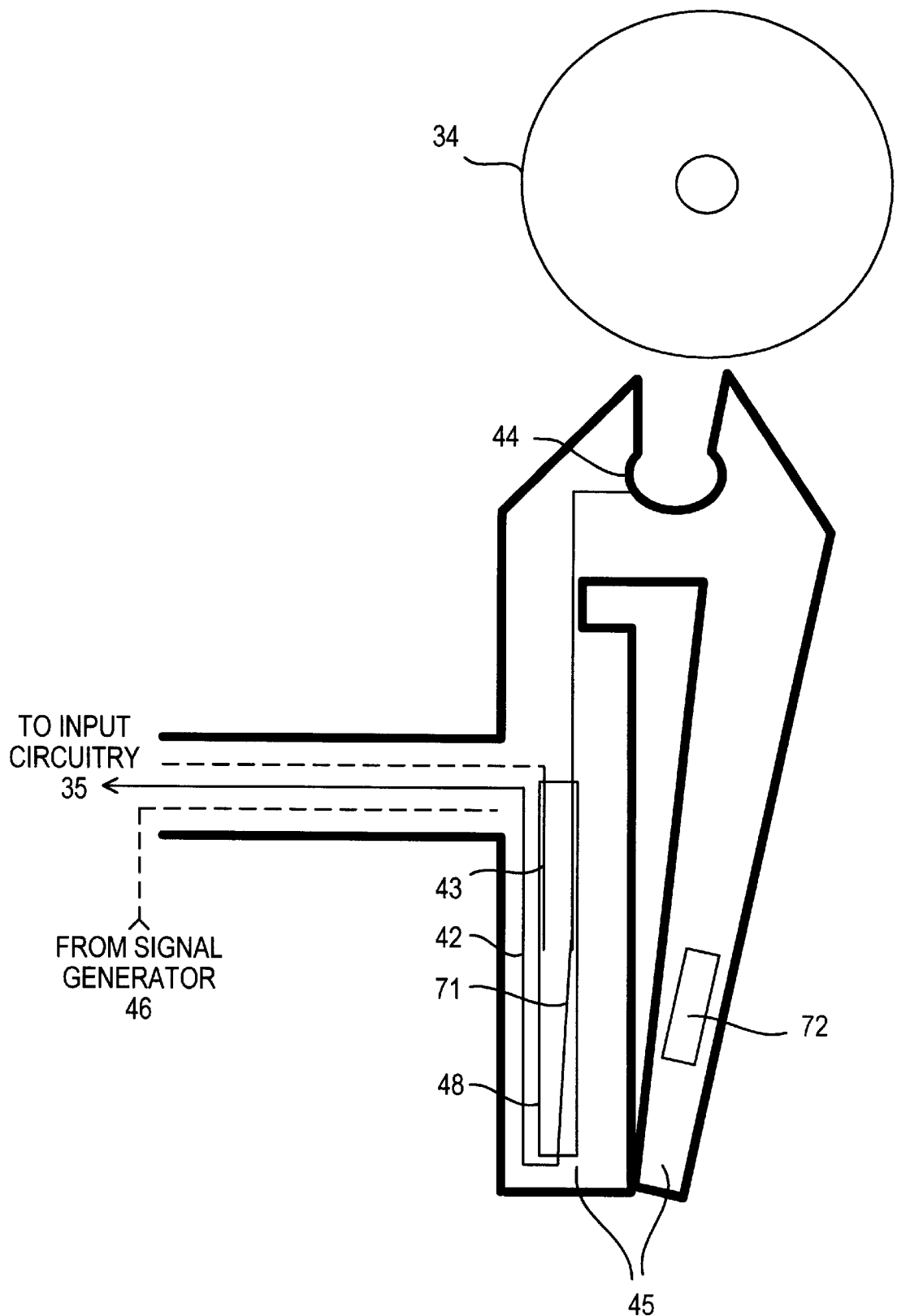
FIG. 7B illustrates the clip according to FIG. 7A incorporating the magnetic reed switch in the active mode.
Figure 7C:
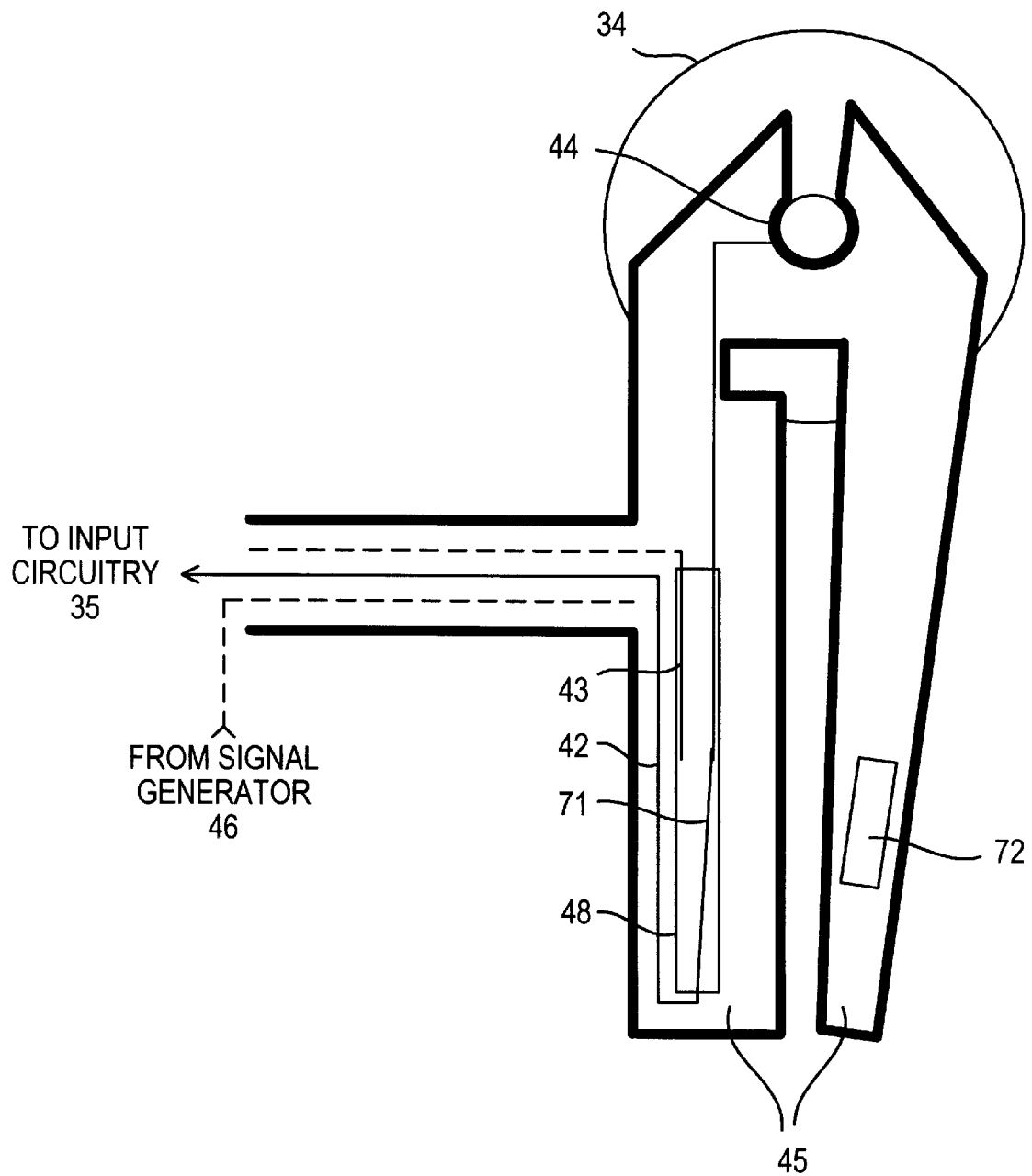
FIG. 7C illustrates the clip according to FIG. 7A incorporating the magnetic reed switch in the active mode and the clip connected to an electrode.
Figure 8A:
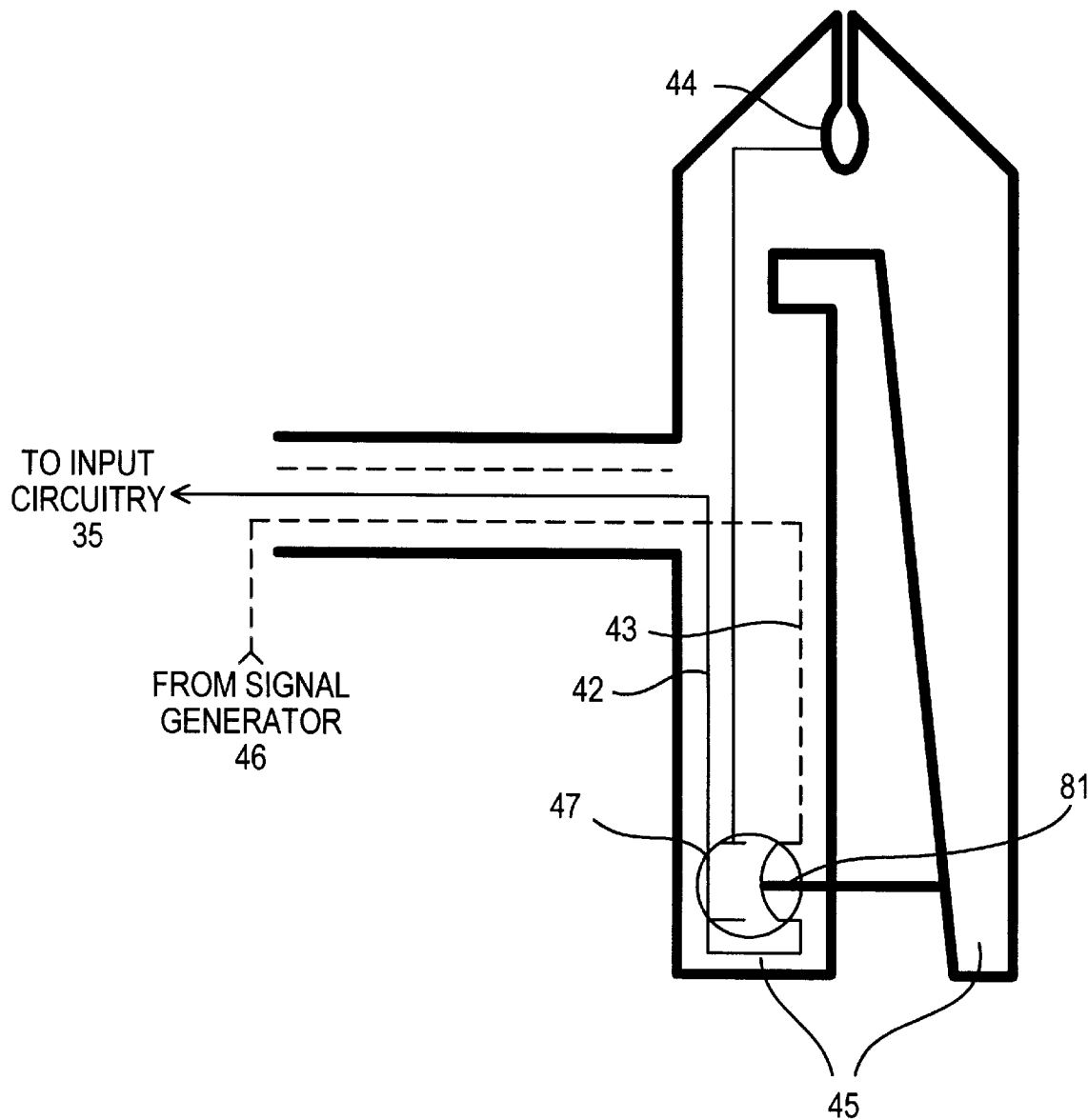
FIG. 8A illustrates another embodiment of a clip according to the present invention incorporating a button switch in the inactive mode.
Figure 8B:
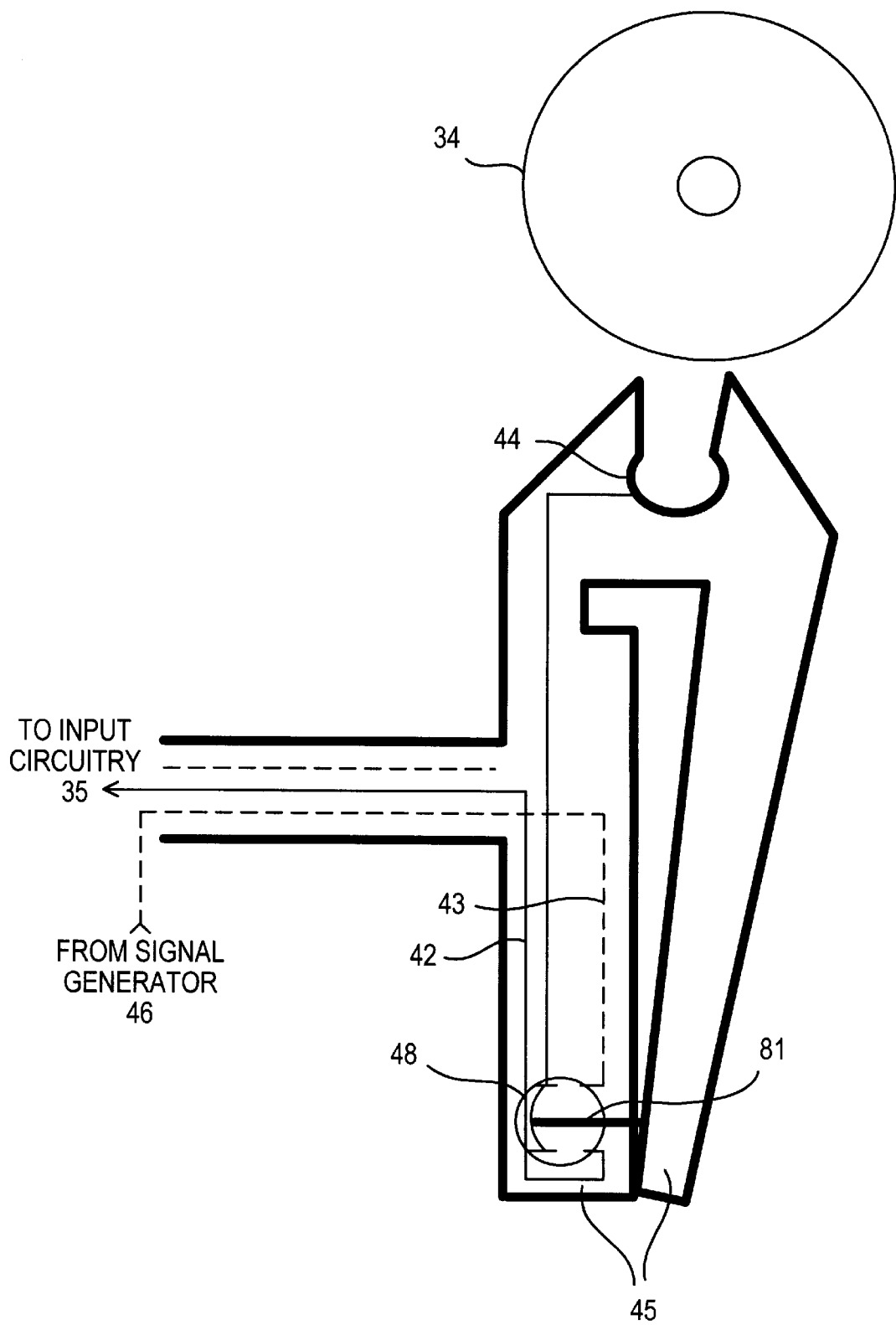
FIG. 8B illustrates the clip according to FIG. 8A incorporating a button switch in the active mode.
Figure 8C:
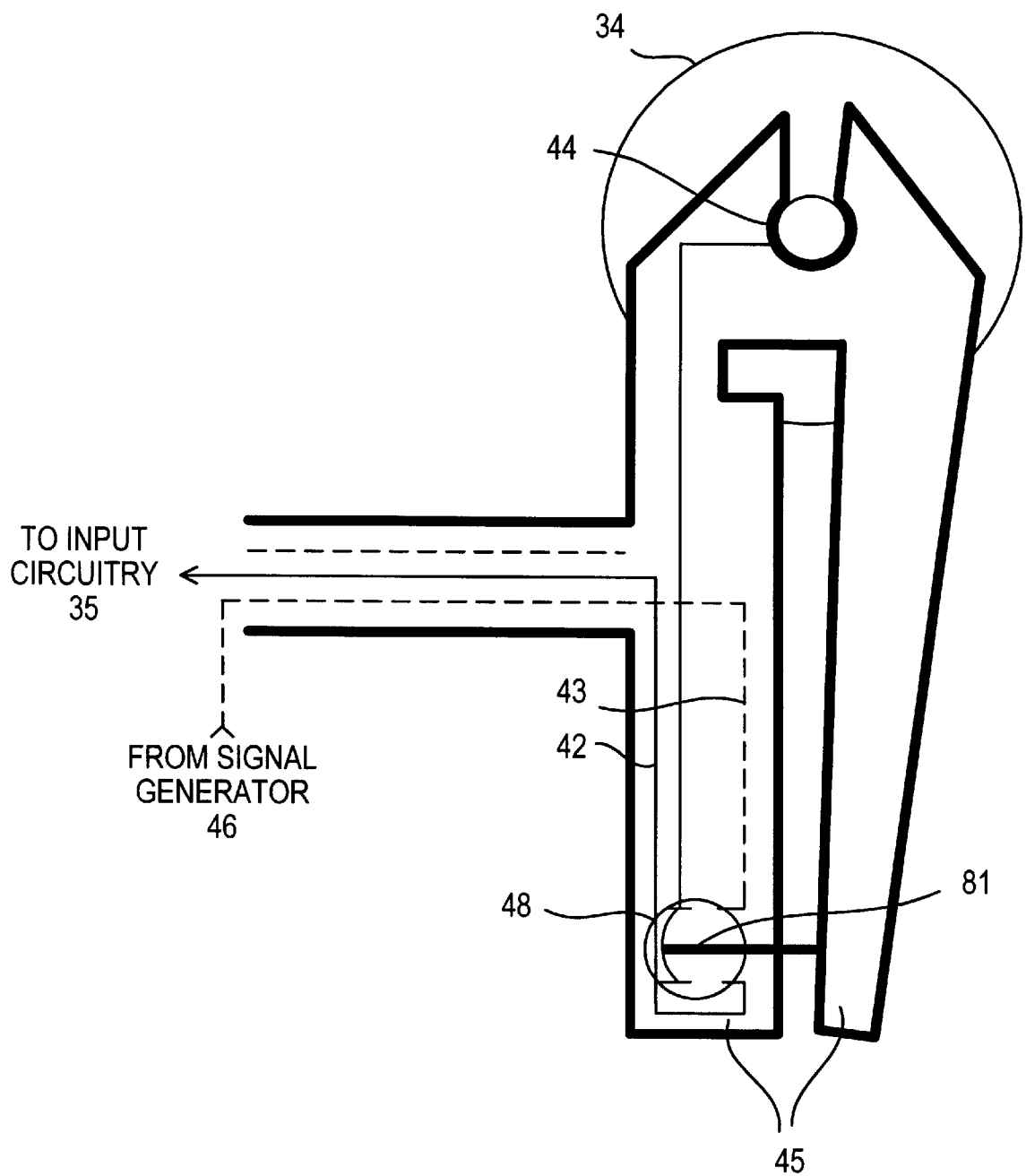
FIG. 8C illustrates the clip according to FIG. 8A incorporating a button switch in the active mode and the clip connected to an electrode.

The clips 40 of the present invention may include other types of switches such as a magnetic reed switch 71 integrated into the clip 70 as shown in FIGS. 7A–7C or a push button switch 81 integrated into the clip 80 as shown in FIGS. 8A–8C.

Referring to FIGS. 7A–7C, the clip 70 includes a magnetic reed switch 71 and magnet 72 which may be molded to the clip 70. The magnetic reed switch 71 remains in the inactive mode 47 until adequate pressure is placed on the handle 45 placing the magnet 72 in close proximity to the magnetic reed switch 71 which switches the magnetic reed switch 71 to the active mode 48, as shown in FIGS. 7B and 7C.

Referring to FIG. 8A, the button switch 81 remains in the inactive mode 47 until adequate pressure is placed on the handle 45 in which the button switch 81 switches to the active mode 48, as shown in FIGS. 8B and 8C. Similar to the pin switch 41 in FIGS. 4A–4C, the magnetic reed switch 71 and the button switch 81 connect the input line 42 to the shield 43 in the inactive mode 47 and connect the input line 42 to the electrode connector 44 in the active mode 48.

Figure 9:
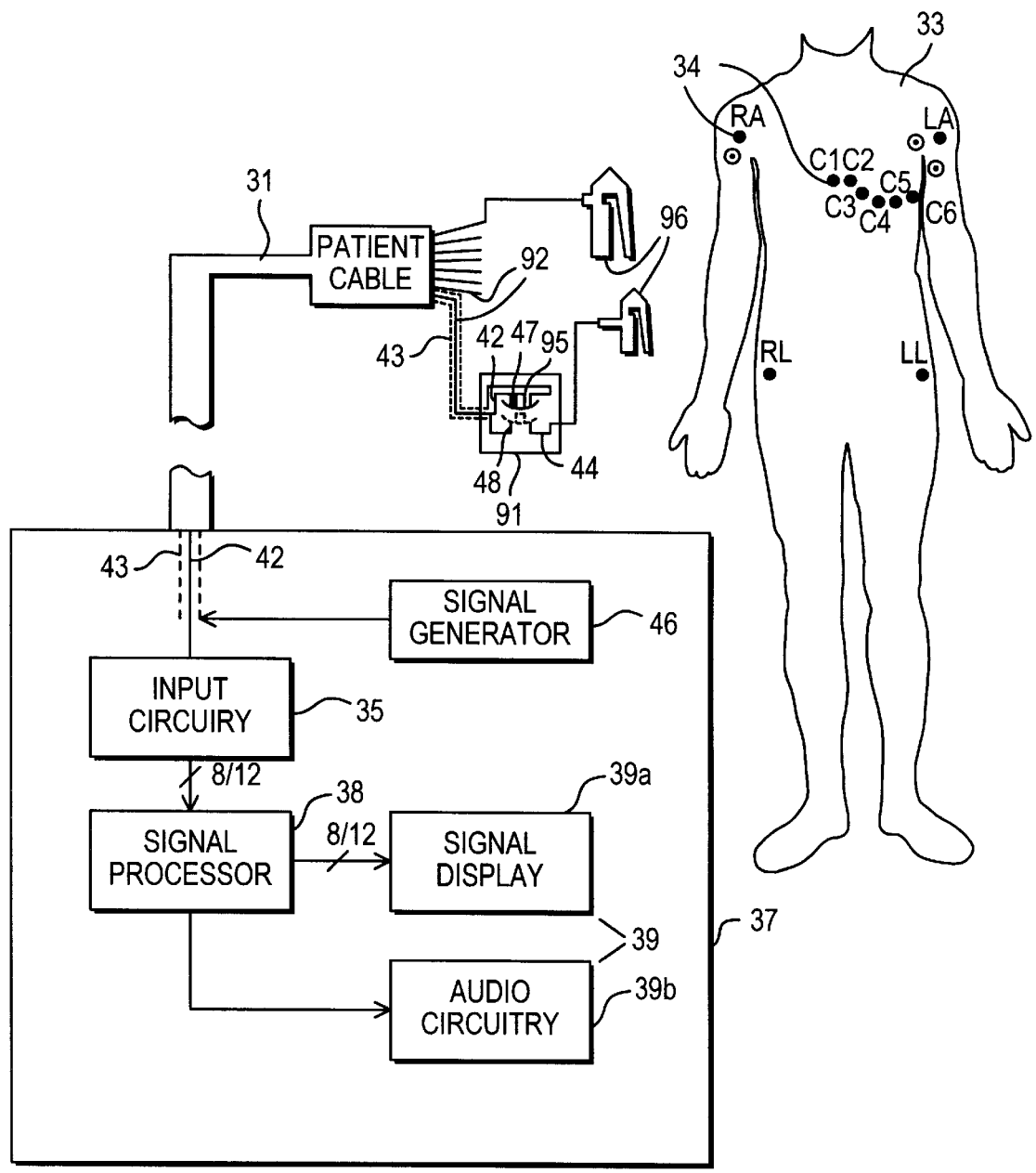
FIG. 9 illustrates a second embodiment of the present invention.

FIG. 9 illustrates a second embodiment of the present invention. As shown in FIG. 9, each of the plurality of leads 92 of the patient cable 31 includes a switch 91. Unlike the first embodiment as shown in FIG. 3, the switch 91 is not an integrated part of the clip 40. Further, the switch 91 has an activation portion 95 which is activated by an operator. The switch 91 connects the input line 42 to the shield 43 in an inactive mode 47 shown in solid lines. The switch 91 connects the input line 42 to the electrode connector 44 of the typical clip 96 in an active mode 48, as shown by dotted lines. Referring to FIG. 9, the lead protection and identification system of the second embodiment also includes a notification device 39 for providing information to a user indicating to which one of the plurality of electrodes 34 the active lead 92 should be connected. The notification device 39 provides the information to the user when the activation portion 95 of one of the plurality of switches 91 is activated and the switch 91 switches from an inactive mode 47 to an active mode 48. In one embodiment, the activation portion 95 of the switch 91 is a button. The button may be activated by a user adequately pressing the button, that is, the user must apply enough force to cause the switch 91 to switch from the inactive mode 47 to the active mode 48.

Figure 10:
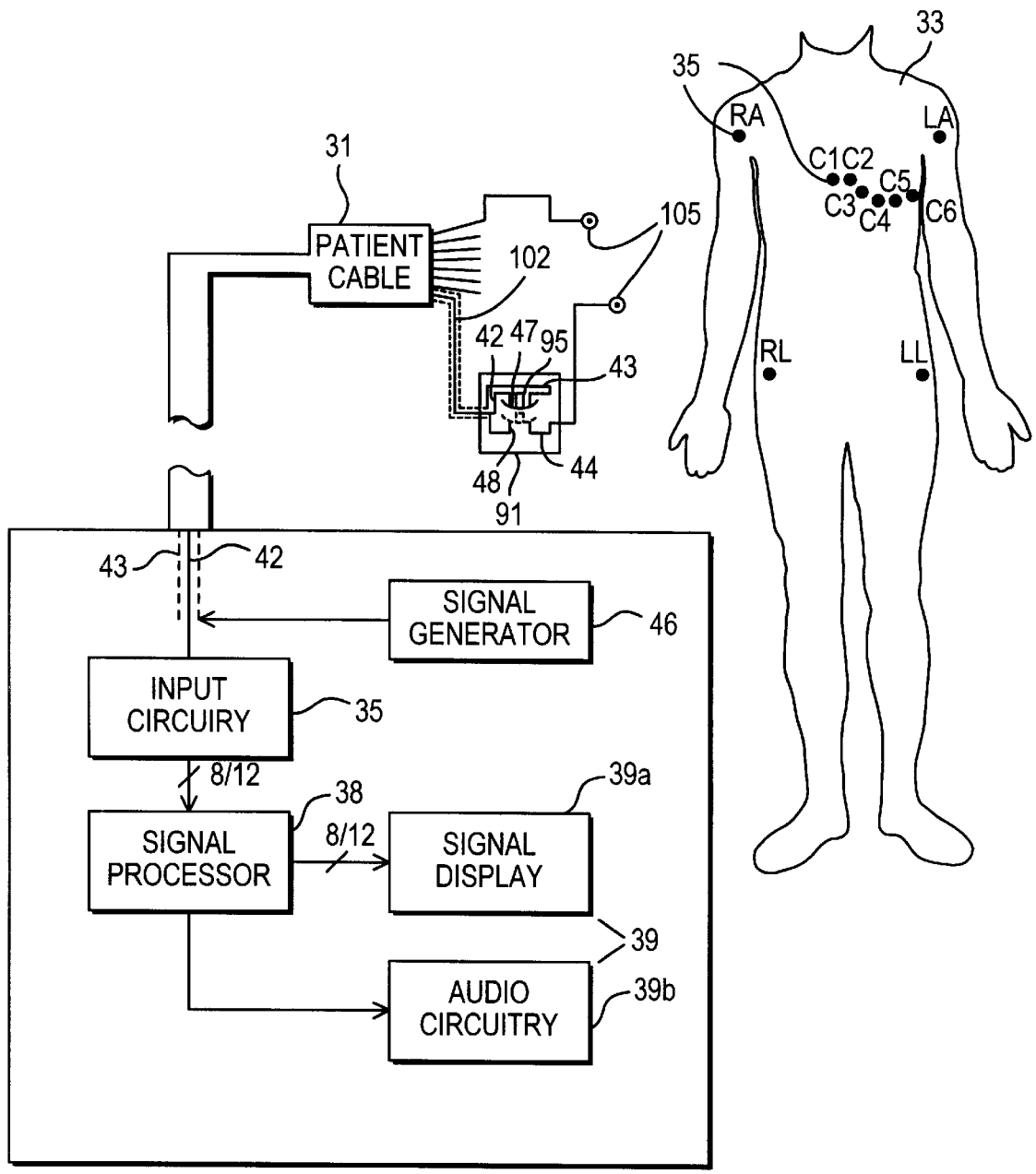
FIG. 10 illustrates a third embodiment of the present invention.

FIG. 10 illustrates a third embodiment of the present invention. As shown in FIG. 10, the electrode detection system includes a patient cable 31. Each of the plurality of cables 102 of the patient cable 31 includes an electrode 105. Unlike the second embodiment shown in FIG. 9, the leads 102 do not include clips 36 because the electrodes 105 are already directly connected to the cables 102. Each of the plurality of electrodes 105 are adapted to be placed at predetermined locations 34 on a patient 33. According to this embodiment of the present invention, instead of informing the operator of which electrode to place the active lead clip on, the present embodiment informs the operator of the precise location on the patient that the active lead electrode should be placed. The notification device 39 provides the information to the user when the activation portion 95 of the switch 91 is activated and the switch 91 switches from an inactive mode 47 to an active mode 48.

Although the diagnostic device 37 has been shown as including signal generator 46, input circuitry 35, signal processor 38 and notification device 39, each of the above-mentioned devices can be included as a separate device. That is, the above-mentioned devices can be constructed as one unit or several units including any combination of the above-mentioned devices.

The embodiments described above are illustrative examples of the present invention and it should not be construed that the present invention is limited to these particular embodiments. Various changes and modifications may be effected by one skilled in the art without departing from the spirit or scope of the invention as defined in the appended claims.

What is claimed is:

1. A lead identification system comprising:

a medical diagnostic device;

a plurality of electrodes;

a patient cable having a first end connected to said medical diagnostic device and a second end including a plurality of cables;

a plurality of clips each attached to a corresponding one of said plurality of cables, each clip comprising an input line, a shield, a switch, a handle, and an electrode connector, said switch operable by said handle and connecting said input line to said shield in an inactive mode, and connecting said input line to said electrode connector in an active mode;

a signal generator for providing a predetermined signal to said shield of each clip;

a signal analyzer for analyzing a signal based on said predetermined signal present on each said input line and outputting an analyzing result; and a notification device for receiving the analyzing result output by said signal analyzer and for providing information to an operator as to which of said plurality of electrodes a given clip should be attached to, based on the analyzing result, said notification device providing said information to the operator when said handle of one of said plurality of clips is pressed and said switch goes from an inactive mode to an active mode, permitting said electrode connector to engage one of said plurality of electrodes.

2. The lead identification system according to claim 1, wherein said information provided by said notification device is an audio message.

3. The lead identification system according to claim 1, further comprising a display, wherein said information provided by said notification device is a visual message displayed on said display.

4. The lead identification system according to claim 1, wherein said switch is one of a pin switch, button switch, and magnetic reed switch, integrated with said clip.

5. The lead identification system according to claim 4, wherein said switch is said magnetic reed switch, and each of said plurality of clips further includes a magnet which communicates with said magnetic reed switch to allow said magnetic reed switch to go between said inactive mode and active mode.

6. The lead identification system according to claim 1, wherein said patient cable is one of a 12-lead electrocardiogram cable and an 8-lead vector electrocardiogram cable.

7. A lead protection and identification system for a medical diagnostic device, the medical diagnostic device including a patient cable having a first end and a second end, wherein the first end connects to said medical diagnostic device and the second end includes a plurality of cables, each of said plurality of cables respectively connects to one of a plurality of electrodes, said plurality of electrodes adapted to be placed on predetermined locations of a patient, the lead protection and identification system comprising:

a plurality of clips each comprising an input line, a shield, a switch, a handle, and an electrode connector, said switch operable by said handle and connecting said input line to said shield in an inactive mode, and connecting said input line to said electrode connector in an active mode;

a signal generator for providing an input signal to said shield allowing the switch to selectively cause a characteristic event to occur on said input line;

an identifier for identifying which one of said plurality of clips is in said active mode based upon the occurrence of the characteristic event of said input line;

a notification device for providing information to a user as to which one of said plurality of clips should be connected to which one of said plurality of electrodes based on an output from the identifier;

wherein said switch of said clip prevents potentially dangerous signals from being inputted to said clip when said clip is not connected to said electrode.

8. The lead protection and identification system according to claim 7, further comprising an audio device, wherein said information provided by said notification device is an audio message output by said audio device.

9. The lead protection and identification system according to claim 7, further comprising a display, wherein said information provided by said notification device is a visual message displayed on said display.

10. The lead protection and identification system according to claim 7, wherein said switch is one of a pin switch, button switch, and magnetic reed switch, integrated with said clip.

11. The lead protection and identification system according to claim 10, wherein said switch is said magnetic reed switch, and said plurality of clips further includes a magnet which communicates with said magnetic reed switch to allow said magnetic reed switch to go between an inactive mode and active mode.

12. The lead protection and identification system according to claim 7, wherein said patient cable is one of a 12-lead electrocardiogram cable and an 8-lead vector electrocardiogram cable.

* * * * *